United States Patent
Szewczyk

(10) Patent No.: US 9,084,871 B2
(45) Date of Patent: Jul. 21, 2015

(54) PROCESS FOR MANUFACTURING A FLEXIBLE ELONGATE STRUCTURE HAVING AN ORIENTABLE END

(75) Inventor: Jérôme Szewczyk, Vienne en Arthies (FR)

(73) Assignees: UNIVERSITE PIERRE ET MARIE CURIE (PARIS 6), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 408 days.

(21) Appl. No.: 13/636,208

(22) PCT Filed: Mar. 24, 2011

(86) PCT No.: PCT/EP2011/001472
§ 371 (c)(1),
(2), (4) Date: Sep. 20, 2012

(87) PCT Pub. No.: WO2011/116961
PCT Pub. Date: Sep. 29, 2011

(65) Prior Publication Data
US 2013/0000100 A1    Jan. 3, 2013

(30) Foreign Application Priority Data
Mar. 24, 2010    (FR) ...................... 10 52119

(51) Int. Cl.
| | |
|---|---|
| *A61M 31/00* | (2006.01) |
| *B21D 39/00* | (2006.01) |
| *A61M 25/01* | (2006.01) |
| *A61B 1/00* | (2006.01) |
| *A61B 1/005* | (2006.01) |
| *A61M 25/02* | (2006.01) |

(52) U.S. Cl.
CPC .......... *A61M 25/0133* (2013.01); *A61B 1/0011* (2013.01); *A61B 1/0053* (2013.01); *A61B 1/0055* (2013.01); *A61B 1/0056* (2013.01); *A61B 1/0057* (2013.01); *A61B 1/00078* (2013.01); *A61M 25/0105* (2013.01);
(Continued)

(58) Field of Classification Search
CPC ............. A61B 1/0051; A61M 25/0158; C08L 2201/12; H01H 37/323; H01H 37/50
USPC ..................................... 604/95.05
See application file for complete search history.

(56) References Cited

U.S. PATENT DOCUMENTS 4,753,223 A * 6/1988 Bremer .................. 600/140
4,790,624 A * 12/1988 Van Hoye et al. ............ 385/118
(Continued)

FOREIGN PATENT DOCUMENTS

WO    95/06494 A1    3/1995

OTHER PUBLICATIONS

International Search Report of PCT/EP2011/001472 dated Jun. 29, 2011.

*Primary Examiner* — Jacob Cigna
(74) *Attorney, Agent, or Firm* — Sughrue Mion, PLLC

(57) ABSTRACT

A method of fabricating an elongate structure having a steerable end, the structure including a flexible longitudinal body associated with at least one actuator member having at least one shape memory alloy wire or "SMAW" extending along the body and anchored thereto at its ends, and associated with a mechanism for heating it in controlled manner. The method includes the following steps: inserting at least one of the ends of the SMAW in tubes; crimping the tubes onto the ends of the SMAW; and securing the tubes to the body in such a manner that the wire extends along the body.

6 Claims, 2 Drawing Sheets

(52) U.S. Cl.
CPC .. *A61M2025/028* (2013.01); *A61M 2025/0213* (2013.01); *Y10T 29/49908* (2015.01)

(56) References Cited

U.S. PATENT DOCUMENTS

| | | | |
|---|---|---|---|
| 4,944,727 A | 7/1990 | McCoy | |
| 5,025,799 A * | 6/1991 | Wilson | 600/585 |
| 5,090,956 A * | 2/1992 | McCoy | 604/95.05 |
| 5,135,517 A * | 8/1992 | McCoy | 604/531 |
| 6,672,338 B1 * | 1/2004 | Esashi et al. | 138/119 |
| 7,416,534 B2 * | 8/2008 | Nair et al. | 600/585 |
| 2010/0069882 A1 * | 3/2010 | Jennings et al. | 604/525 |
| 2010/0168666 A1 * | 7/2010 | Tegg | 604/95.04 |

* cited by examiner

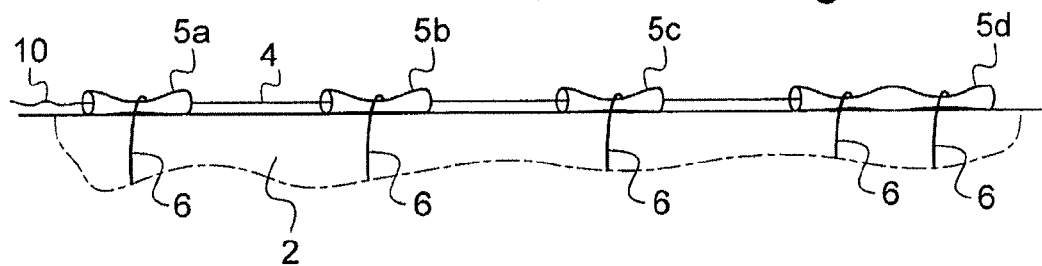
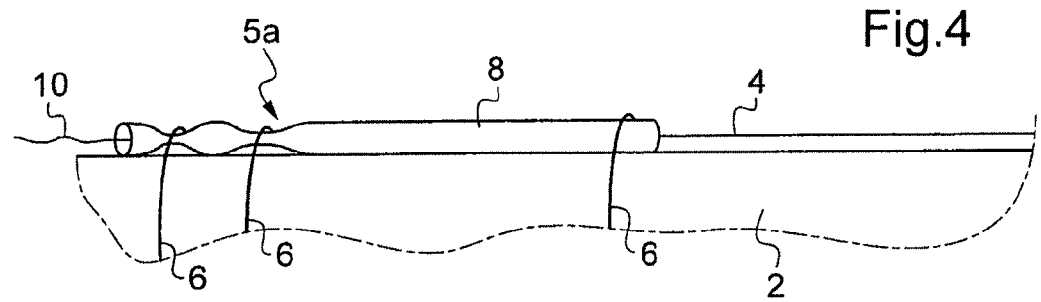
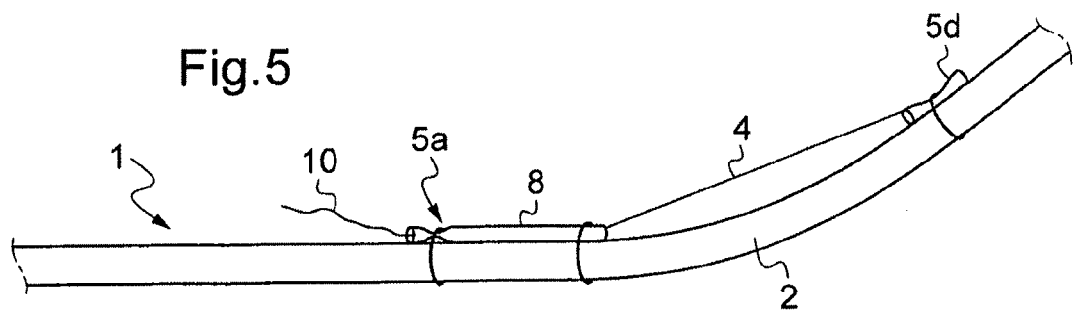

PROCESS FOR MANUFACTURING A FLEXIBLE ELONGATE STRUCTURE HAVING AN ORIENTABLE END

CROSS REFERENCE TO RELATED APPLICATIONS

This application is a National Stage of International Application No. PCT/EP2011/001472 filed Mar. 24, 2011, claiming priority based on French Patent Application No. 1052119 filed Mar. 24, 2010, the contents of all of which are incorporated herein by reference in their entirety.

The present invention relates to a method of fabricating a flexible elongate structure having a steerable end.

The invention is advantageously applicable in the field of medicine and more particularly for making an endoscope or a catheter.

Nevertheless, although it is particularly designed for medical applications, the invention may equally well be used in a variety of other technical fields that make use of elongate structures having steerable ends, such as non-destructive inspection of pipes.

BACKGROUND OF THE INVENTION

In known manner, surgeons prefer to use techniques that are not very invasive, making use of narrow access paths in order to treat vascular diseases. Such techniques make it possible to limit recourse to open surgery and they are therefore less burdensome for the patient. For this purpose, use is often made of a catheter or an endoscope that possesses at its end a steerable elongate body for the purpose of facilitating insertion and advance of the elongate body inside the human body.

The structure of the elongate body includes at least one actuator member enabling its end to be curved so as to enable it to negotiate bends and move into non-rectilinear portions of the human body, or indeed in order to view and to treat portions of the body that are not located on the main axis of the elongate body.

Various types of actuator member have been proposed, some of which use shape memory alloy wires (referred to below as SMAWs).

The SMAWs extend along the elongate body, with their ends being anchored thereto. The SMAWs are associated with means for heating them, e.g. by the Joule effect, thereby causing them to contract in order to cause the elongate body to bend. For this purpose, electrical power supply wires are connected to the SMAWs.

Nevertheless, such structures are difficult to fabricate. The SMAW must both be fastened at its ends to the longitudinal body and must also be connected to the power supply wire.

Various ways of securing SMAWs to the body have been proposed, such as adhesive or indeed lasers, but they are not very satisfactory since they do not make it possible to guarantee both that the wire is accurately positioned on the longitudinal body and that it is properly held over time, in particular given the large variations of temperature in the SMAW, and the high traction forces to which the SMAW is subjected.

It is important to emphasize that the positioning of the wire is particularly important when the longitudinal body carries a plurality of SMAWs, since it is necessary to prevent any contact between these wires in order to avoid short circuits.

Finally, it should also be observed that the extra thickness due to the SMAWs and to the means for connecting the SMAWs to the body must be minimized so that the assembly presents the compactness needed to enable the structure to pass along ducts of small diameters.

OBJECT OF THE INVENTION

The present invention seeks to propose an improvement to such steerable longitudinal structures including SMAW actuators.

SUMMARY OF THE INVENTION

To this end, the invention provides a method of fabricating an elongate structure having a steerable end, the structure comprising a flexible longitudinal body associated with at least one actuator member comprising at least one shape memory alloy wire or "SMAW" extending along the body and anchored thereto at its ends, the SMAW being associated with means for heating it in controlled manner.

According to the invention, the method comprises the following steps:
  inserting the SMAW in tubes including at least two end tubes;
  crimping at least the end tubes onto the ends of the SMAW; and
  securing the tubes to the body in such a manner that the wire extends along the body.

Thus, the use of crimped tubes facilitates manipulating the SMAW while it is being positioned along the body, without running the risk of the SMAW being damaged while it is being put into place.

This technique avoids the SMAW being subjected to any welding, soldering, or adhesive. The crimping deforms the outside surfaces of the tubes, thus serving, in particular if the tubes are connected to the body by ligatures, to improve the strength of the connection between the tubes and the body, relative to the traction forces generated by contraction of the SMAW.

In addition, the tube may be selected to be electrically conductive and may thus be connected to the electrical power supply wire, thus making it easier for the SMAW to be electrically connected to the electrical power supply wire.

In another aspect of the invention, intermediate tubes are provided between the end tubes that are crimped to the ends of the SMAW, the intermediate tubes also being secured to the body and optionally being crimped onto the SMAW.

This characteristic makes it possible to obtain greater curvature of the portion of the longitudinal body that extends between the end tubes, and consequently makes it easier for the practitioner to steer and move the longitudinal structure.

BRIEF DESCRIPTION OF THE DRAWINGS

The present invention can be better understood on reading a detailed description of an embodiment given with reference to the accompanying drawings that are provided by way of non-limiting example, and in which:

FIG. 3 is a fragmentary longitudinal section view of an elongate structure in a second embodiment of the invention; and FIGS. 4 and 5 are fragmentary longitudinal section views of a variant embodiment of a longitudinal structure shown in a rest position and in a curved position.

DETAILED DESCRIPTION OF THE INVENTION

Figure 1:
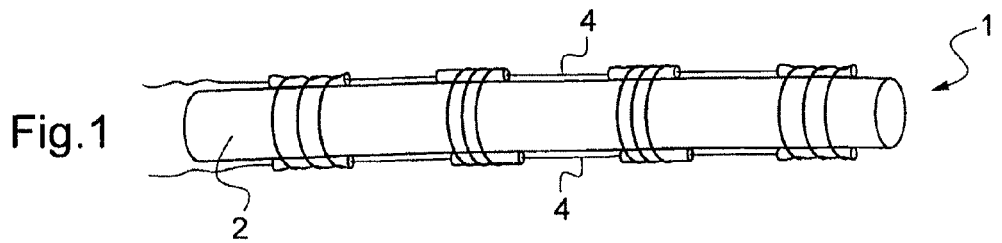
FIG. 1 is a perspective view of an elongate structure with a steerable end in a particular embodiment of the invention.

FIG. 1 shows a longitudinal structure 1 with a steerable end comprising a flexible longitudinal body 2 associated with an actuator member that includes an SMAW 4 extending along the body 2. The SMAW extends inside a certain number of tubes 5a, 5b, 5c, 5d that are secured to the body 2 by ligaments 7. In this example, all of the tubes are crimped on the SMAW 4. The tubes are electrically conductive, and the end tubes 5a and 5d are connected to electrical power supply wires enabling the SMAW 4 to be heated by the Joule effect, thereby causing it to contract and thus causing the portion of the body 2 along which the SMAW 4 extends to bend.

Figures 2A, 2B:
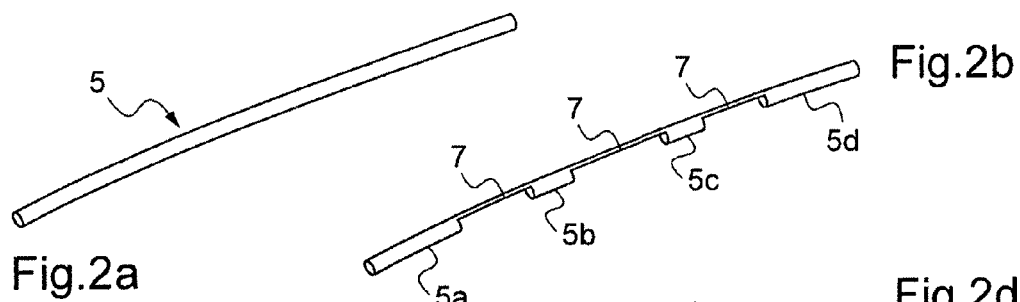
FIGS. 2a to 2g are fragmentary longitudinal section views of the FIG. 1 elongate structure with a steerable end, during different steps in its fabrication.
Figures 2C, 2D:
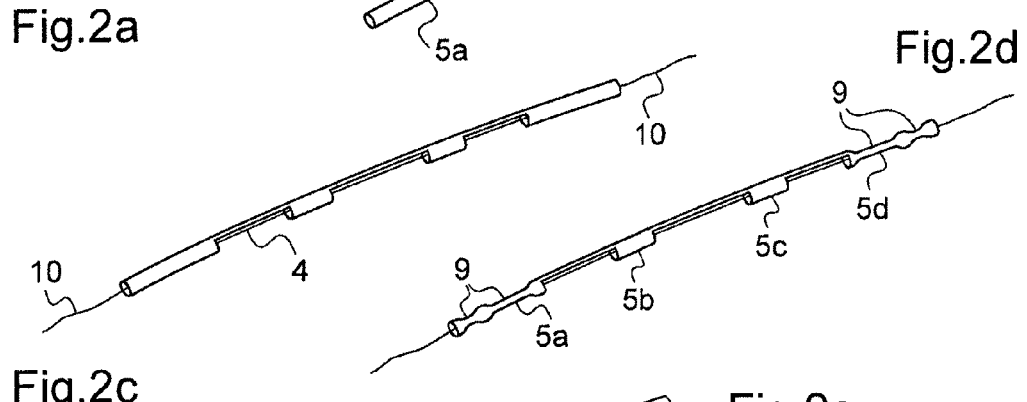

In a first mode of fabrication having steps that are shown in FIGS. 2a to 2g, the starting material is a sheath 5 of rigid conductive material, the sheath is cut out as shown in FIG. 2b so as to leave tubular segments 5a to 5d that are connected together by ligaments 7. Then, as can be seen in FIG. 2c, the SMAW 4 is put into place inside the tubes 5 so that the SMAW extends through all of the tubes, and then the electrical power supply wires 10 are put into place by engaging their ends in the end tubes 5a and 5d, respectively.

Then, as can be seen in FIG. 2d, the end tubes 5a and 5d are crimped onto the wires 4 and 10, thereby forming a succession of indentations 9 and projections thereon. Thereafter, as can be seen in FIG. 2e, the assembly made in this way is fitted against the body 2.

Figures 2E, 2F:
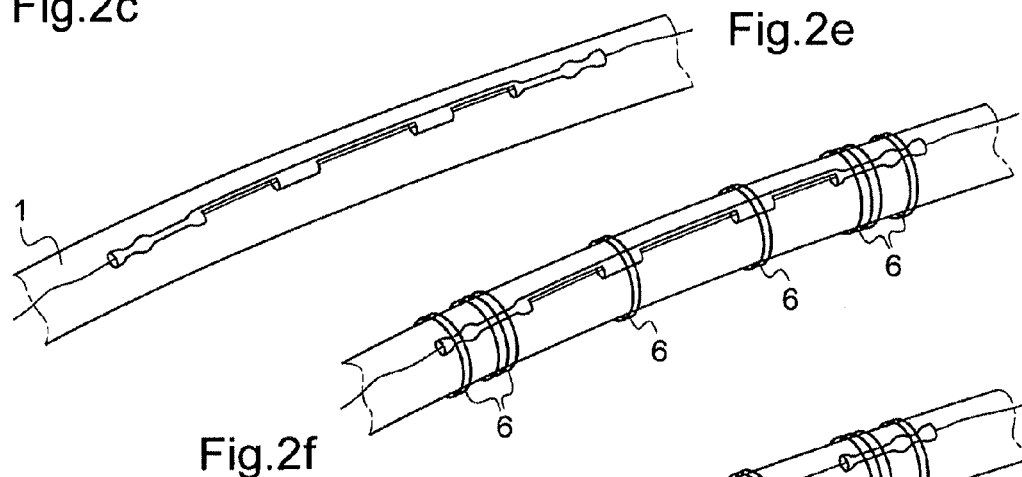

As shown in FIG. 2f, the assembly is secured to the body 2 by means of ligatures 6 that extend to clamp against the tubes 5a, 5b, 5c, and 5d. It can be seen that for the end tubes 5a and 5d, the ligatures 6 extend in the crimping indentations 9, thereby preventing said tubes from moving axially relative to the body 2.

Figure 2G:
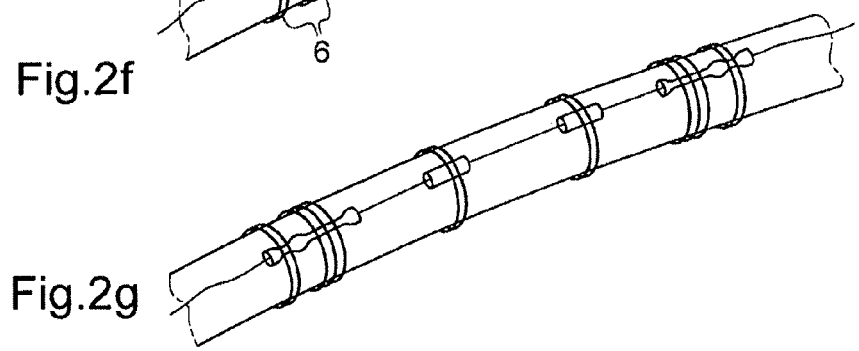

Finally, as shown in FIG. 2g, the ligaments 7 are removed, leaving behind only the tubes 5a to 5d of the initial sheath. This ensures that the tubes are properly in alignment with one another while they are being secured to the flexible longitudinal body 2.

In this embodiment, the end tubes 5a and 5d are crimped onto the ends of the SMAW 4 thus serving to anchor it on the body 2. They also provide electrical connections between the SMAW 4 and the electrical power supply wires 10. In contrast the intermediate tubes 5b and 5c form journals for guiding the SMAW 4 during its controlled contractions and expansions.

This embodiment may be subjected to numerous variants, some of which are shown in FIGS. 3 and 4.

As shown in FIG. 3, the ligatures 6 may clamp a plurality of tubes each associated with a distinct SMAW 4. In addition, the intermediate tubes may themselves be crimped onto the SMAW 4.

As shown in FIG. 4, a tubular portion 8 of the sheath may be allowed to remain so as to extend one of the tubes in order to stiffen the body 2 locally. As shown in this figure, a tubular portion 8 has been allowed to remain that extends the tube 5a, and the end of the portion is attached by ligature to the body 2. Thus, and as can be seen in FIG. 5, during contraction of the SMAW 4, the body 2 can no longer bend in register with the tubular portion 8, but only in the portions along which the SMAW is left free of any guidance. Thus, an extension in the form of a tubular portion 8 contributes to reducing the radius of curvature of the body while it is bending since the bending becomes concentrated in the above-mentioned portions, for a given length of SMAW.

Naturally, the end tubes 5a and 5d may be extended inwardly, i.e. towards the other tubes as shown in the figures, or outwardly. Similarly, it is possible to extend the intermediate tubes.

Preferably, the length of the extension 8 is less than five times the diameter of the longitudinal body 2 so that its overall flexibility remains sufficient to avoid hindering progress of the body 2.

The invention is not limited to the above description, but on the contrary covers any variant coming within the ambit defined by the claims.

In particular, although it is stated above that the tubes are secured to the body by ligatures, it is possible to use other securing means, such as adhesive.

Although it is stated that the tubes are made of an electrically conductive material, this is not essential even though it does facilitate making connections between the SMAW and the electrical power supply wires. If the tubes are of a diameter that is sufficient to enable the SMAW and a corresponding power supply wire to be superposed inside each of the end tubes, then electrical contact is established between them by the pressure applied by the crimping.

Although it is stated above that the tubes are made by being cut out from a common sheath, which greatly facilitates manipulation of the SMAW and its positioning on the body of the structure, it is possible instead to make use of a plurality of tubes through which a single SMAW is threaded and including at least two end tubes.

The invention claimed is:

1. A method of fabricating an elongate structure having a steerable end, the structure comprising a flexible longitudinal body associated with at least one actuator member comprising at least one shape memory alloy wire or "SMAW" extending along the body and comprising two ends, the SMAW being anchored to the body at the two ends of the SMAW, the SMAW being associated with means for heating the SMAW in a controlled manner, wherein the method comprises the following steps:
   inserting the SMAW in tubes including at least two end tubes;
   crimping at least the end tubes onto the ends of the SMAW; and
   securing the tubes to the body in such a manner that the wire extends along the body;
   wherein the tubes are all obtained by being cut out from a common sheath; and
   wherein the sheath is cut so as to leave the tubes connected together by ligaments, the tubes as connected together by ligaments then being secured to the body before the ligaments are eliminated.

2. A method according to claim 1, wherein the means for heating comprises electrical power supply wires, ends of the electrical power supply wires being inserted in the end tubes.

3. A method according to claim 1, wherein at least one of the tubes is provided with an extension beyond a crimped portion.

4. A method according to claim 1, wherein the tubes are connected to the body by ligatures.

5. A method according to claim 4, wherein, for the crimped tubes, the ligatures extend in indentations left by the crimping of said tubes.

6. A method of fabricating an elongate structure having a steerable end, the structure comprising a flexible longitudinal body associated with at least one actuator member comprising at least one shape memory alloy wire or "SMAW" extending along the body and comprising two ends, the SMAW being anchored to the body at the two ends of the SMAW, the SMAW associated with electrical power supply wires that heat the SMAW in a controlled manner, wherein the method comprises the following steps:

inserting the SMAW in tubes including at least two end tubes;
crimping at least the end tubes onto the ends of the SMAW; and
securing the tubes to the body in such a manner that the wire extends along the body;
wherein the tubes are all obtained by being cut out from a common sheath; and
wherein the sheath is cut so as to leave the tubes connected together by ligaments, the tubes as connected together by ligaments then being secured to the body before the ligaments are eliminated.

* * * * *